US009603555B2

United States Patent
Horng et al.

(10) Patent No.: US 9,603,555 B2
(45) Date of Patent: *Mar. 28, 2017

(54) MOTION/VIBRATION DETECTION SYSTEM AND METHOD WITH SELF-INJECTION LOCKING

(71) Applicants: INDUSTRIAL TECHNOLOGY RESEARCH INSTITUTE, Hsinchu (TW); NATIONAL SUN YAT-SEN UNIVERSITY, Kaohsiung (TW)

(72) Inventors: Tzyy-Sheng Horng, Kaohsiung (TW); Fu-Kang Wang, Kaohsiung (TW); Kang-Chun Peng, Kaohsiung (TW)

(73) Assignees: INDUSTRIAL TECHNOLOGY RESEARCH INSTITUTE, Hsinchu (TW); NATIONAL SUN YAT-SEN UNIVERSITY, Kaohsiung (TW)

( * ) Notice: Subject to any disclaimer, the term of this patent is extended or adjusted under 35 U.S.C. 154(b) by 637 days.

This patent is subject to a terminal disclaimer.

(21) Appl. No.: 14/154,252

(22) Filed: Jan. 14, 2014

(65) Prior Publication Data

US 2014/0123763 A1 May 8, 2014

Related U.S. Application Data

(63) Continuation-in-part of application No. 14/151,930, filed on Jan. 10, 2014, now Pat. No. 9,375,153, which
(Continued)

(30) Foreign Application Priority Data

May 17, 2010 (TW) .............................. 99115691 A
Oct. 12, 2011 (TW) ............................ 100136990 A
(Continued)

(51) Int. Cl.
*G01B 9/02* (2006.01)
*A61B 5/113* (2006.01)
(Continued)

(52) U.S. Cl.
CPC .............. *A61B 5/113* (2013.01); *A61B 5/024* (2013.01); *A61B 5/0816* (2013.01); *G01H 3/00* (2013.01);
(Continued)

(58) Field of Classification Search
CPC .......... G01H 9/00; G01H 3/00; A61B 5/0017; A61B 5/7228; A61B 5/725; A61B 5/1102
See application file for complete search history.

(56) References Cited

U.S. PATENT DOCUMENTS 3,221,260 A  11/1965 Henrion
3,479,607 A  11/1969 Ruthroff
(Continued)

FOREIGN PATENT DOCUMENTS

CN  1800876  7/2006
CN  101006915  8/2007
(Continued)

OTHER PUBLICATIONS

Final Office Action issued in U.S. Appl. No. 14/151,930, filed Jan. 10, 2014, mailed Nov. 25, 2015.
(Continued)

*Primary Examiner* — Harshad R Patel
*Assistant Examiner* — Samir M Shah
(74) *Attorney, Agent, or Firm* — McClure, Qualey & Rodack, LLP

(57) ABSTRACT

A motion/vibration detection system and method therefore are provided. The system includes a transmitter and a receiver. The transmitter includes a transmit/receive antenna unit and a first oscillator. The receiver includes a receiving
(Continued)

unit and a demodulation unit. The transmit/receive antenna unit receives an output signal from the first oscillator and transmits a detection signal. The detection signal is reflected from at least one object under detection into a reflected detection signal, which is received by the transmit/receive antenna unit. The transmit/receive antenna unit injects the reflected detection signal into the first oscillator and accordingly the first oscillator is under a self-injection locking mode. The receiving unit receives the detection signal. The demodulation unit demodulates the detection signal received by the receiving unit into a baseband output signal, to extract at least one motion/vibration information of the objection under detection.

24 Claims, 7 Drawing Sheets

Related U.S. Application Data is a continuation-in-part of application No. 13/456,849, filed on Apr. 26, 2012, now Pat. No. 8,754,772, which is a continuation-in-part of application No. 12/886,522, filed on Sep. 20, 2010, now Pat. No. 8,698,636.

(60) Provisional application No. 61/751,978, filed on Jan. 14, 2013.

(30) Foreign Application Priority Data

Mar. 18, 2013 (TW) .............................. 102109406 A
May 13, 2013 (TW) .............................. 102116921 A

(51) Int. Cl.
| A61B 5/024 | (2006.01) |
| A61B 5/08 | (2006.01) |
| G01H 3/00 | (2006.01) |
| A61B 5/11 | (2006.01) |
| A61B 5/00 | (2006.01) |
| A61B 5/05 | (2006.01) |

(52) U.S. Cl.
CPC ............ A61B 5/0002 (2013.01); A61B 5/0059 (2013.01); A61B 5/02416 (2013.01); A61B 5/05 (2013.01); A61B 5/1102 (2013.01); A61B 5/725 (2013.01); A61B 5/7257 (2013.01)

(56) References Cited

U.S. PATENT DOCUMENTS

| 3,670,327 | A | 6/1972 | Marsh |
| 4,109,247 | A | 8/1978 | Kaplan |
| 4,123,755 | A | 10/1978 | Fishbein et al. |
| 4,176,351 | A | 11/1979 | DeVita et al. |
| 4,427,982 | A | 1/1984 | Caprio |
| 4,517,982 | A | 5/1985 | Shiga et al. |
| 4,600,890 | A | 7/1986 | Horvat |
| 4,646,754 | A | 3/1987 | Seale et al. |
| 4,951,060 | A | 8/1990 | Cohn |
| 4,953,010 | A | 8/1990 | Cowley |
| 4,958,638 | A | 9/1990 | Sharpe et al. |
| 4,991,585 | A | 2/1991 | Mawhinney |
| 5,243,992 | A | 9/1993 | Eckerle et al. |
| 5,423,076 | A | 6/1995 | Westergren et al. |
| 5,458,123 | A | 10/1995 | Unger |
| 5,458,124 | A | 10/1995 | Stanko et al. |
| 5,573,012 | A | 11/1996 | McEwan et al. |
| 5,650,749 | A | 7/1997 | Main |
| 5,975,081 | A | 11/1999 | Hood et al. |
| 6,133,802 | A | 10/2000 | Ma et al. |
| 6,369,647 | B1 | 4/2002 | Main et al. |
| 6,369,659 | B1 | 4/2002 | Delzer |
| 6,650,276 | B2 | 11/2003 | Lawless |
| 6,756,936 | B1* | 6/2004 | Wu .......................... G01S 7/032 |
| | | | 342/175 |
| 6,858,006 | B2 | 2/2005 | MacCarter et al. |
| 7,103,132 | B1 | 9/2006 | Baba |
| 7,314,451 | B2 | 1/2008 | Halperin et al. |
| 7,538,718 | B2 | 5/2009 | Ikeda et al. |
| 7,616,148 | B2 | 11/2009 | Wu et al. |
| 7,656,208 | B2 | 2/2010 | Kimura et al. |
| 7,740,588 | B1 | 6/2010 | Sciarra |
| 7,753,849 | B2 | 7/2010 | Morgan et al. |
| 7,848,896 | B2 | 12/2010 | Li et al. |
| 8,092,389 | B2 | 1/2012 | Keilman et al. |
| 8,103,228 | B2 | 1/2012 | Monat et al. |
| 8,562,526 | B2 | 10/2013 | Heneghan et al. |
| 8,754,772 | B2* | 6/2014 | Horng ...................... A61B 5/11 |
| | | | 340/539.1 |
| 9,375,153 | B2* | 6/2016 | Horng ................ G08B 13/2491 |
| 9,423,496 | B2* | 8/2016 | Horng ...................... G01S 13/08 |
| 2004/0150548 | A1 | 8/2004 | Walmsley |
| 2005/0063034 | A1* | 3/2005 | Maleki .................... H03B 17/00 |
| | | | 359/245 |
| 2005/0073424 | A1 | 4/2005 | Ruoss et al. |
| 2005/0285790 | A1 | 12/2005 | Gagnon |
| 2006/0040739 | A1 | 2/2006 | Wells |
| 2006/0055585 | A1 | 3/2006 | Nagasaku |
| 2007/0047970 | A1 | 3/2007 | Tsuji |
| 2007/0126511 | A1 | 6/2007 | Jacobsson et al. |
| 2007/0200648 | A1* | 8/2007 | Reichenbach ........... H01Q 3/26 |
| | | | 333/133 |
| 2007/0241864 | A1 | 10/2007 | Nagai |
| 2008/0068251 | A1* | 3/2008 | Meinecke ............... G01S 13/34 |
| | | | 342/112 |
| 2008/0077015 | A1 | 3/2008 | Boric-Lubecke et al. |
| 2008/0079636 | A1 | 4/2008 | Mohamadi |
| 2008/0119716 | A1 | 5/2008 | Boric-Lubecke et al. |
| 2008/0146944 | A1 | 6/2008 | Tao et al. |
| 2008/0183053 | A1 | 7/2008 | Borgos et al. |
| 2009/0160697 | A1 | 6/2009 | Wu |
| 2009/0203972 | A1 | 8/2009 | Heneghan et al. |
| 2009/0243850 | A1 | 10/2009 | Nishizato |
| 2009/0264761 | A1 | 10/2009 | Keilman et al. |
| 2009/0278728 | A1 | 11/2009 | Morgan et al. |
| 2009/0290066 | A1 | 11/2009 | Lin |
| 2010/0151799 | A1 | 6/2010 | Kim et al. |
| 2010/0152600 | A1 | 6/2010 | Droitcour et al. |
| 2010/0198083 | A1* | 8/2010 | Lin .......................... A61B 5/05 |
| | | | 600/484 |
| 2010/0240999 | A1 | 9/2010 | Droitcour et al. |
| 2010/0249630 | A1 | 9/2010 | Droitcour et al. |
| 2010/0259305 | A1 | 10/2010 | Lee et al. |
| 2011/0026443 | A1* | 2/2011 | Okada ...................... H01P 1/17 |
| | | | 370/280 |
| 2011/0137189 | A1 | 6/2011 | Kuo et al. |
| 2011/0148884 | A1 | 6/2011 | Zeleny |
| 2011/0215879 | A1 | 9/2011 | Aratake |
| 2011/0279275 | A1 | 11/2011 | Horng et al. |
| 2012/0021698 | A1 | 1/2012 | Borlez et al. |
| 2012/0022348 | A1 | 1/2012 | Droitcour et al. |
| 2012/0209087 | A1* | 8/2012 | Horng ...................... A61B 5/11 |
| | | | 600/301 |
| 2012/0235689 | A1* | 9/2012 | Jau ...................... A61B 5/0205 |
| | | | 324/629 |
| 2013/0234729 | A1* | 9/2013 | Jau ...................... G08B 13/2491 |
| | | | 324/642 |
| 2014/0016731 | A1 | 1/2014 | Okada et al. |

FOREIGN PATENT DOCUMENTS

| CN | 101049239 | 10/2007 |
| CN | 101093995 | 12/2007 |
| CN | 101489478 A | 7/2009 |
| CN | 102247146 A | 11/2011 |
| CN | 102499686 A | 6/2012 |
| TW | 373153 | 11/1999 |

(56) References Cited

FOREIGN PATENT DOCUMENTS

| TW | 200706158 | | 2/2007 |
|---|---|---|---|
| TW | 200913524 | A | 3/2009 |
| TW | 201120790 | | 6/2011 |
| TW | I347108 | | 8/2011 |
| TW | 201143312 | | 12/2011 |
| WO | 2006115704 | A1 | 11/2006 |

OTHER PUBLICATIONS

Nang, et al.: "Single-Antenna Doppler Radars Using Self and Mutual Injection Locking for Vital Sign Detection With Random Body Movement Cancellation"; IEEE Transactions on Microwave Theory A='ID Techniques, vol. 59, No. 12, Dec. 2011; pp. 3577-3587.
Kaneyuki Kurokawa: "Injection Locking of Microwave Solid-State Oscillators"; Proceedings of the IEEE, vol. 61, No. 10, Oct. 1973; pp. 1386-1410.
Heng-Chia Chang: "Phase Noise 1n Self-Injection-Locked Oscillators—Theory and Experiment"; IEEE Transactions on Microwave Theorgy and Techniques, vol. 51, No. 9, Sep. 2003; 1994-1999.
TW Office Action dated Jan. 5, 2015 in corresponding Taiwan application (No. 102109406).
Non-Final Office Action issued in U.S. Appl. No. 14/151,930, filed Jan. 10, 2014, dated Mar. 13, 2015.
SIPO Office Action dated Feb. 5, 2016 in corresponding Chinese application (No. 201310236231.8).
TW Office Action dated Jul. 11, 2014.
TW Office Action dated Aug. 8, 2014.
Wang, et al.: "Mutual Injection-Locked SIL Sensor Array for Vital Sign Detection with Random Body Movement Cancellation"; Dept. of EE, National Sun Yat-Sen University, Kaohsiung, 804, TW; copyright 2011; pp. 1-4.
Full English machine translation of CN1800876 (Published Jul. 12, 2006).
Full English machine translation of CN101006915 (Published Aug. 1, 2007).
Full English machine translation of CN101049239 (Published Oct. 10, 2007).
English Abstract translation of TW373153 (Published Nov. 1, 1999).
English Abstract translation of TWI347108 (Published Aug. 11, 2011).
English Abstract translation of TW200706158 (Published Feb. 16, 2007).
Chattopadhyay, et al.: "Short Papers"; IEEE Transactions on Microwave Theory and Techniques, vol. MTT-34, No. 4, Apr. 1986; pp. 442-446.
Chuang, et al.: "60-GHz Millimeter-Wave Life Detection System (MLDS) for Noncontact Human Vital-Signal Monitoring"; IEEE Sensors Journal, vol. 12, No. 3, Mar. 2012; pp. 602-609.
Biswas, et al.: "A Doubly Tracking Discriminator"; 978-1-4244-4819-7/09/$25.00 © 2009 IEEE.
Chin, et al.: "A Fast Clutter Cancellation Method in Quadrature Doppler Radar for N oncontact Vital Signal Detection"; 978-1-4244-7732-6/101$26.00 © 201 0 IEEE; pp. 764-767.
A. Singh, V. M. Lubecke; "A Heterodyne Receiver for Harmonic Doppler Radar Cardio-pulmonary Monitoring with Body-worn Passive RF Tags"; THPD: Biological Effects and Medical Applications of RF and Microwave; IMS 2010 Abstract Cards.
Chattopadhyay, et al.: "A New Microwave Discriminator"; 0-7803-8114-9/03/$17.00 02003 IEEE; pp. 1078-1081.
Wang, et al.: "A Novel Vital-Sign Sensor Based on a Self-Injection-Locked Oscillator"; IEEE Transactions on Microwave Theory and Techniques, vol. 58, No. 12, Dec. 2010; pp. 4112-4120.
Chen, et al.: "An X-Banc Microwave Life-Detection System"; IEEE Transactions on Biomedical Engineering, vol. BME-33, No. 7, Jul. 1986; pp. 697-701.
Park, et al.: "Arctangent Demodulation With DC Offset Compensation in Quadrature Doppler Radar Receiver Systems"; IEEE Transactions on Microwave Theory and Techniques, vol. 55, No. 5, May 2007; pp. 1073-1079.
Main, et al.: "FM Demodulation Using an Injection-Locked Oscillator"; TU3A-1; 0-7803-5687-X/00/$10.000 2000 IEEE; 2000 IEEE MIT-S Digest; pp. 135-138.
Xiao, et al.: "Frequency-Tuning Technique for Remote Detection of Heartbeat and Respiration Using Low-Power Double-Sideband Transmission in the Ka-Band"; IEEE Transactions on Microwave Theory and Techniques, vol. 54, No. 5, May 2006; pp. 2023-2032.
Tarar, et al.: "Injection-Locked Phase-Locked Loop for BPSK Coherent Demodulation: Theory and Design"; 1-4244-1449-0/07/ $25.00 © 2007 IEEE; pp. 387-390.
Fletcher, et al.: "Low-Cost Differential Front-End for Doppler Radar Vital Sign Monitoring"; 978-1-4244-2804-5/09/$25.00 © 2009 IEEE; pp. 1325-1328.
Lin JC: "Microwave sensing of physiological movement and volume change: a review."; Department of Electrical Engineering and Computer Science, University of Illinois, Chicago 60680; 1992;13(6):557-65.
Pan, et al.: "Null point elimination using RF phase shifter in continuous-wave Doppler radar system"; Electronics Letters Oct. 13, 2011 vol. 47 No. 21.
Droitcour, et al.: "Range Correlation and I/Q Performance Benefits in Single-Chip Silicon Doppler Radars for Noncontact Cardiopulmonary Monitoring";IEEE Transactions on Microwave Theory and Techniques, vol. 52, No. 3, Mar. 2004; pp. 838-848.
Girbau, et al.: "Remote Sensing of Vital Signs Using a Doppler Radar and Diversity to Overcome Null Detection"; IEEE Sensors Journal, vol. 12, No. 3, Mar. 2012; pp. 512-518.
Wang, et al.: "Combining SIL Tag and IL Receiver for Concurrent Vital Sign and Position Sensing"; 978-1-4673-2141-9/13/$31.00 © 2013 IEEE.
CN Office Action dated Jul. 28, 2015 in corresponding Chinese application (No. 201310118801.3).

\* cited by examiner

MOTION/VIBRATION DETECTION SYSTEM AND METHOD WITH SELF-INJECTION LOCKING

This is a CIP (continuation-in-part) application of U.S. application Ser. No. 14/151,930 filed on Jan. 10, 2014, entitled "MOTION/VIBRATION SENSOR," which claims the benefit of Taiwan application Serial No. 102109406 filed Mar. 18, 2013. The U.S. application entitled "MOTION/VIBRATION SENSOR" is a CIP application of U.S. application Ser. No. 13/456,849, filed Apr. 26, 2012, which claims the benefit of Taiwan application Serial No. 100136990, filed Oct. 12, 2011. The U.S. application Ser. No. 13/456,849, filed Apr. 26, 2012 is a CIP of U.S. application Ser. No. 12/886,522, filed Sep. 20, 2010 which claims the benefit of Taiwan application Serial No. 099115691, filed May 17, 2010. This application also claims the benefit of priority from U.S. Provisional Patent Application No. 61/751,978, filed Jan. 14, 2013, and Taiwan application Serial No. 102116921, filed May 13, 2013. All of the above-listed disclosures are incorporated by reference herein in their entireties.

TECHNICAL FIELD

The disclosure relates in general to a motion/vibration detection system and a method applicable thereto.

BACKGROUND

Under the influence of social trend in aging population, medical care service and bio-medical electronic devices attract more attention. Remote homecare combined with wireless communication is capable of sensing and recording bio-physiology signals of patients without staying in hospital to save medical resources.

In bio-physiology signal detection, breath signals and heartbeat signals are very important because they can be used in long term tracking for OSAS (Obstructive Sleep Apnea Syndrome) and irregular heartbeat symptom. The physiology signal sensing mechanism could be used in the motion/vibration detection of objects present in the environment, and also could be used in the security monitoring or identification of persons present in the environment.

Currently, contact type and non-contact type bio-physiology signal sensing apparatuses are used. The contact bio-physiology signal sensing apparatuses perform measurement by touching people's body.

A microwave motion sensor compares phase difference between a transmission signal and a receiving signal based on Doppler theory. If the phase difference varies with time, it indicates that there is a moving or vibrating object in the environment.

Therefore, the disclosure provides a motion/vibration sensor which detects vibration of thoracic cavity of a user under measurement to analyze bio-physiology parameters (such as breath and heartbeat frequencies) of the user under measurement or detects external vibrator information (for example, mechanical vibration frequency).

SUMMARY

The disclosure is directed to a motion/vibration detection system and a method applicable thereto.

In an exemplary embodiment, the disclosed relates to a motion/vibration detection system. The system comprises at least one transmitter, and at least one receiver. The transmitter at least includes a transmit/receive antenna unit and a first oscillator. The receiver at least includes a receiving unit and a demodulation unit. The transmit/receive antenna unit, is coupled to or electrically connected to a signal output port of the first oscillator, receives an output signal from the first oscillator and sends a detection signal (STX). The detection signal is reflected by at least one object into a reflected detection signal (SRX), which is received by the transmit/receive antenna unit. The transmit/receive antenna unit injects the reflected detection signal (SRX), as an injection signal, into the first oscillator and accordingly the first oscillator is under a self-injection locking mode. The receiving unit is coupled to or electrically connected to the demodulation unit and receives the detection signal (STX). The demodulation unit demodulates the detection signal (STX) received by the receiving unit into a baseband output signal, to extract the motion/vibration information of the object under detection.

In another exemplary embodiment, the disclosed relates to a motion/vibration detection method. The method adapted to a motion/vibration detection system. A detection signal is transmitted from a transmitter. The detection signal is reflected by at least one object as at least one reflected detection signal (SRX). The at least one reflected detection signal is received by the transmitter whose oscillator enters into a self-injection locking mode. The detection signal is received by a receiver and demodulated into a baseband output signal, to extract at least one motion/vibration information of the object under detection.

It is to be understood that both the foregoing general description and the following detailed description are exemplary and explanatory only and are not restrictive of the disclosed embodiments, as claimed.

Figure 1:
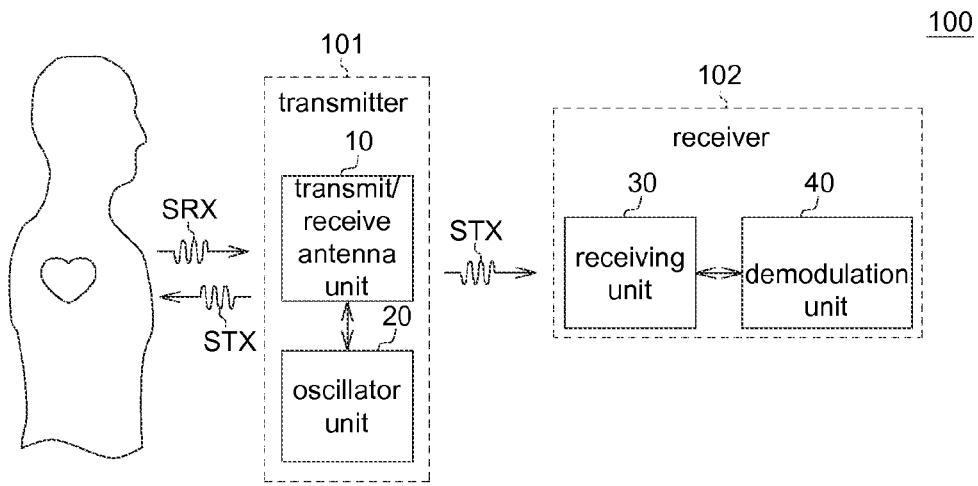
FIG. 1 shows a block diagram of a motion/vibration detection system according to an exemplary embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Technical terms of the disclosure are based on general definition in the technical field of the disclosure. If the disclosure describes or explains one or some terms, definition of the terms is based on the description or explanation of the disclosure. In possible implementation, in the disclosure, the relationship between objects or events includes a direct relationship or an indirect relationship. The indirect relationship refers to that there are intermediate objects or space between the objects or there are intermediate events or timing period between the events. Further, shapes, sizes and ratios of the objects are exemplary for one skilled person in the art to understand the disclosure, not to limit the disclosure.

Each of the disclosed embodiments has one or more technical features. However, it does not mean that implementation of the disclosure needs every technical feature of any embodiment of the disclosure or combination of the embodiments of the disclosure is prohibited. In other words, in possible implementation, one skilled person in the art would selectively implement part or all technical features of any embodiment of the disclosure or selectively combine part or all technical features of the embodiments of the disclosure based on the disclosure of the disclosure and his/her own need. Implementation of the disclosure is flexible.

The disclosure includes a motion/vibration detection system and a method applicable thereto. The technical features of the embodiments of the disclosure are examples for person skilled in the art to understand the disclosure and not to limit the disclosure. Besides, if the implementations are possible, person skilled in the art may choose equivalent elements or steps to implement the disclosure based on the disclosure of the disclosure. That is, the implementation of the disclosure is not limited by the embodiments disclosed in the disclosure.

If the motion/vibration sensor of this disclosure includes one or more known elements, details of the known elements are omitted in the following description if the full disclosure requirement and the enablement requirement are met.

The motion/vibration detection system and method disclosed by the embodiments of the disclosure may be used for detecting motion/vibration information of at least one object under measurement in contact or in non-contact. The object could be a person, a machine, and so on. The signal to be detected could be bio-physiology (for example but not limited to, breath, heartbeat, throat vibration, body vibration, and so on), or motion/vibration signal (for example but not limited to, machine vibrating frequency, and so on). In the following description, a non-contact cardiopulmonary detection on a user is taken as an example but not to limit the disclosure. The contact detection is also suitable in the embodiments.

In the motion/vibration detection system and method according to the embodiments of the disclosure, a user under measurement is detected by transmitting radio frequency waves and/or optical detecting waves. Due to the Doppler effect on the reflection waves, which is caused by the user under measurement and resulted from the bio-physiology behavior (such as breath, heartbeat, throat vibration, body vibration, and so on) of the user under measurement during a detection period, the radio frequency waves and/or the optical detecting waves from the motion/vibration detection system are modulated and the reflected radio frequency waves and/or the optical detecting waves are input into an oscillation unit. Therefore, the oscillator unit is in self-injection locking and the Doppler modulation information of the cardiopulmonary behavior of the user under measurement will be extracted from the oscillator output (for example, by wireless signal processing), to make it easy to observe the cardiopulmonary behavior of the user under measurement.

FIG. 1 shows a functional block diagram for a motion/vibration detection system according to one embodiment of the disclosure. As shown in FIG. 1, the motion/vibration detection system 100 includes, at least, at least one transmitter 101 and at least one receiver 102.

The transmitter 101 includes, at least, a transmit/receive antenna unit 10 and an oscillator unit 20. The transmit/receive antenna unit 10 is coupled to or electrically connected to a signal output port of the oscillator unit 20, receives an output signal from the oscillator unit 20, and transmits a detection signal (STX) to the user. Due to Doppler effect by the user, the detection signal (STX) is modulated into a reflected detection signal (SRX) which is received by the transmit/receive antenna unit 10. The transmit/receive antenna unit 10 injects the reflected detection signal (SRX) as an injection signal, into the oscillator unit 20, so that the oscillator unit 20 is under a self-injection locking mode. The injection path of the injection signal into the oscillator unit 20 could be an injection signal input port or could be one of the output ports of a split signal pair (such as a differential pair) in the oscillator unit 20, so that the oscillator unit 20 is under a self-injection locking mode.

In one embodiment, if the oscillator unit 20 has one single-ended signal output port, then, the transmit/receive antenna unit 10 could be an antenna coupled to or electrically connected to the single-ended signal output port of the oscillator unit 20. The single-ended signal output port could be used as an injection signal input port. That is, the injection signal is injected to the oscillator unit 20 via the single-ended signal output port so that the oscillator unit 20 is under a self-injection locking mode.

In one embodiment, if the oscillator unit 20 has an output differential pair, then, the transmit/receive antenna unit 10 includes a transmitting antenna and a receiving antenna. The transmitting antenna is coupled to or electrically connected to one of the differential pair output ports of the oscillator unit 20. The receiving antenna is coupled to or electrically connected to another of the differential pair output ports of the oscillator unit 20 (i.e. the injection signal is injected via the another port).

In one embodiment, if the oscillator unit 20 is with one single-ended signal output port and an injection signal input port, then, the transmit/receive antenna unit 10 includes a transmitting antenna and a receiving antenna. The transmitting antenna is coupled to or electrically connected to the single-ended signal output port of the oscillator unit 20. The receiving antenna is coupled to or electrically connected to the injection signal input port of the oscillator unit 20.

The receiver 102 includes a receiving unit 30 and a demodulation unit 40. The receiving unit 30 receives the detection signal (STX), and is coupled to or electrically connected to the demodulation unit 40. The demodulation unit 40 is coupled to or electrically connected to the receiving unit 30, and performs frequency demodulation on the received detection signal (STX) into baseband output signals, to extract at least one motion/vibration information of the object under detection (for example, but not limited to, breath, heartbeat, throat vibration, body vibration, etc), or other vibration information (for example, but not limited to, machine vibrating frequency, etc), In one embodiment, the motion/vibration detection system may further include a processing unit which receives the baseband output signal from the demodulation unit. The processing unit processes the baseband output signal, to obtain the time-domain waveforms and frequency-domain signal of the at least one vibration object (for example, the heartbeat of user), for extracting the motion/vibration information (for example, the analysis result of bio-physiology signals) or other external vibration information (for example, the analysis result of vibration signal).

Figure 2:
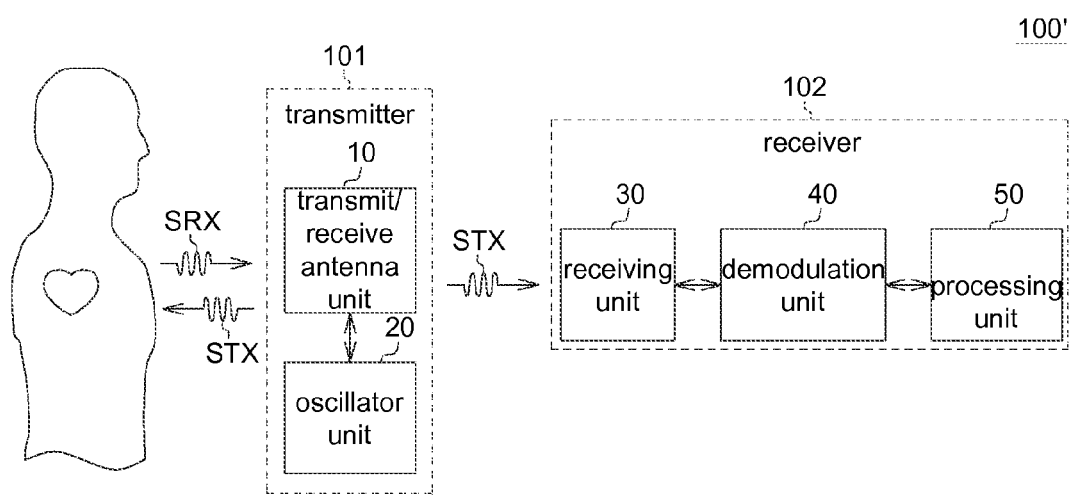
FIG. 2 shows a block diagram of a motion/vibration detection system according to another exemplary embodiment of the disclosure.

FIG. 2 shows a functional block diagram of a motion/vibration detection system 100' according to another embodiment of this disclosure. The motion/vibration detection system 100' further includes a processing unit 50. That is, the processing unit may be not integrated in the motion/vibration detection system (as shown in FIG. 1) or may be integrated in the motion/vibration detection system (as shown in FIG. 2). Further, in other possible embodiment of the disclosure, the processing unit may be at a remote position, and the baseband output signal from the demodulation unit 40 of the motion/vibration detection system may be transmitted to the remote processing unit by wire/wireless transmission, which is still within the scope of the disclosure.

Figure 3:
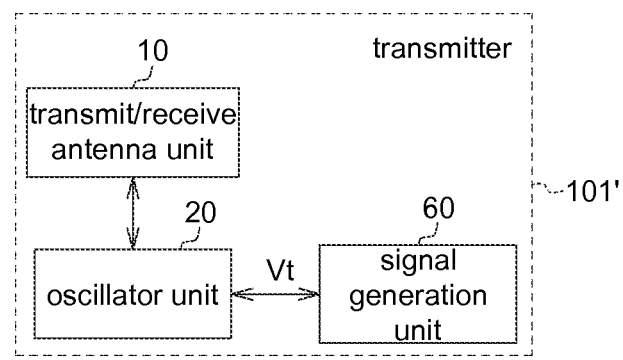
FIG. 3 shows a block diagram of a transmitter according to an exemplary embodiment of the disclosure.

In one embodiment, the transmitter 101' may further include a signal generation unit 60 (as shown in FIG. 3). The output port of the signal generation unit 60 is coupled to or electrically connected to a voltage input port of the oscillator unit 20, to tune an operation frequency of the oscillation unit 20 and thus the oscillator unit 20 generates frequency modulation signals.

In one embodiment, the transmit/receive antenna unit 10 includes an antenna for transmitting a detection signal (STX) and receiving the reflected detection signal (SRX).

In one embodiment, the transmit/receive antenna unit 10 includes a transmitting antenna and a receiving antenna. The transmitting antenna transmits the detection signal (STX) and the receiving antenna receives the reflected detection signal (SRX).

The antenna used in the embodiments of this disclosure could be implemented by a single antenna or an antenna array.

In one embodiment, the receiving unit 30 includes an antenna for receiving the detection signal (STX).

In another embodiment of this disclosure, what is different from the above-described embodiments relies on that the transmit/receive antenna unit 10 includes an optical transmitting device and an optical receiving device. The optical transmitting device is electrically connected to or coupled to the oscillation unit 20 which is an optical laser, for transmitting the optical wave toward the user under measurement. The optical wave is reflected from the user under measurement and received by the optical receiving device. The optical receiving device inputs the reflected optical wave into the oscillation unit 20 which is an optical laser so that the laser is under a self-injection locking mode. The receiving unit 30 includes an optical-to-electrical converter which converts the laser output optical signal into a voltage signal and transmits the voltage signal to the demodulation unit 40.

Figure 4A:
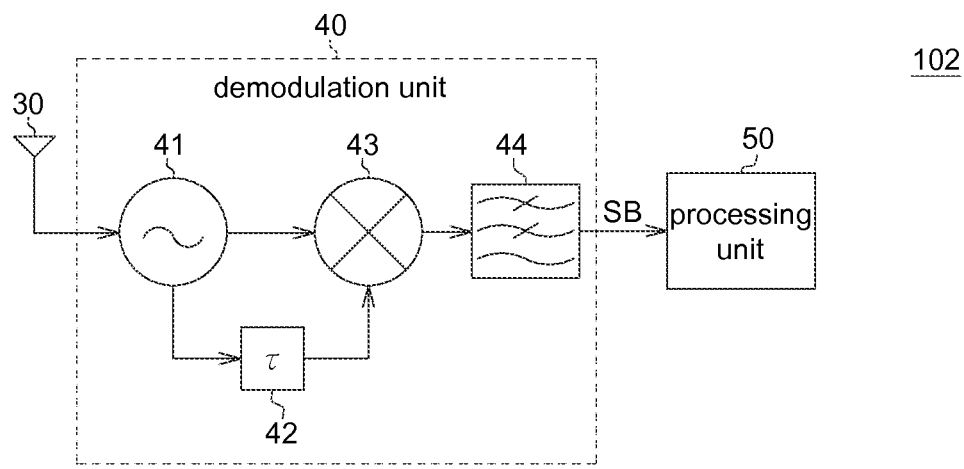
FIG. 4A shows a demodulation unit according to an exemplary embodiment of the disclosure.

In one embodiment, as shown in FIG. 4A, the demodulation unit 40 includes an oscillation unit 41, a time delay unit 42, a mixer unit 43 and a low-pass filter unit 44. The receiving unit 30 is coupled to or electrically connected to the input port of the oscillation unit 41 and injects the detection signal (STX) into the oscillation unit 41, so that the oscillator unit 41 is under a self-injection locking mode.

The output port of the oscillator unit 41 is coupled to or electrically connected to the time delay unit 42 and the mixer unit 43. The two input ports of the mixer unit 43 are coupled to or electrically connected to the output port of the oscillator unit 41 and the output port of the time delay unit 42, respectively. The output port of mixer unit 43 is coupled to or electrically connected to the input port of the low-pass filter unit 44. The mixer unit 43 and the time delay unit 42 demodulates the output signal of the oscillator unit 41. The low-pass filter unit 44 filters out the mixing spurious signals from the output signal of mixer unit 43. The output of the low-pass filter unit 44 is as the baseband output signal SB of the demodulation unit 40. The output signal of the oscillator unit 41 is synchronous with the detection signal (STX) because of injection locking. When the phase difference between two input signals input into the mixer unit 43 is set at odd integer times of 90° by adjusting the time delay of the time delay unit 42, the output signal of the mixer unit 43 contains the analog control voltage waveform Vt and the cardiopulmonary signals of the object under detection. In one embodiment, the oscillator unit 41 includes at least one output port.

Figure 4B:
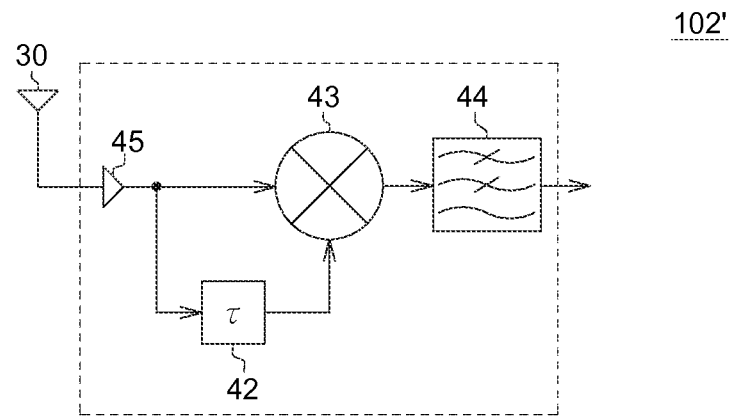
FIG. 4B shows a demodulation unit according to another exemplary embodiment of the disclosure.

In one embodiment, as shown in FIG. 4B, the receiver 102' includes a receiver unit 30 (using antenna as an example), an amplifier unit 45, a mixer unit 43, a time delay unit 42 and a low-pass filter unit 44. The amplifier 45 is coupled or electrically connected to the receiver unit 30. The time delay unit 42 is coupled to or electrically connected to the amplifier unit 45. The two input ports of the mixer unit 43 are coupled to or electrically connected to the amplifier unit 45 and the time delay unit 42. The low-pass filter unit 44 is coupled to or electrically connected to the output port of the mixer unit 43.

Figure 5:
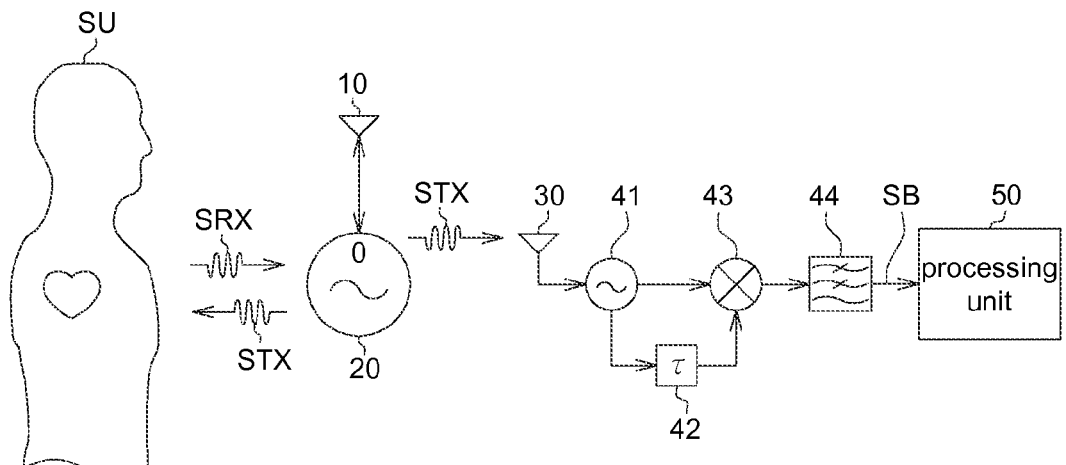
FIG. 5 shows a block diagram of a motion/vibration detection system according to an exemplary embodiment of the disclosure.

FIG. 5 shows the implementation architecture of FIG. 4A.

Figure 4C:
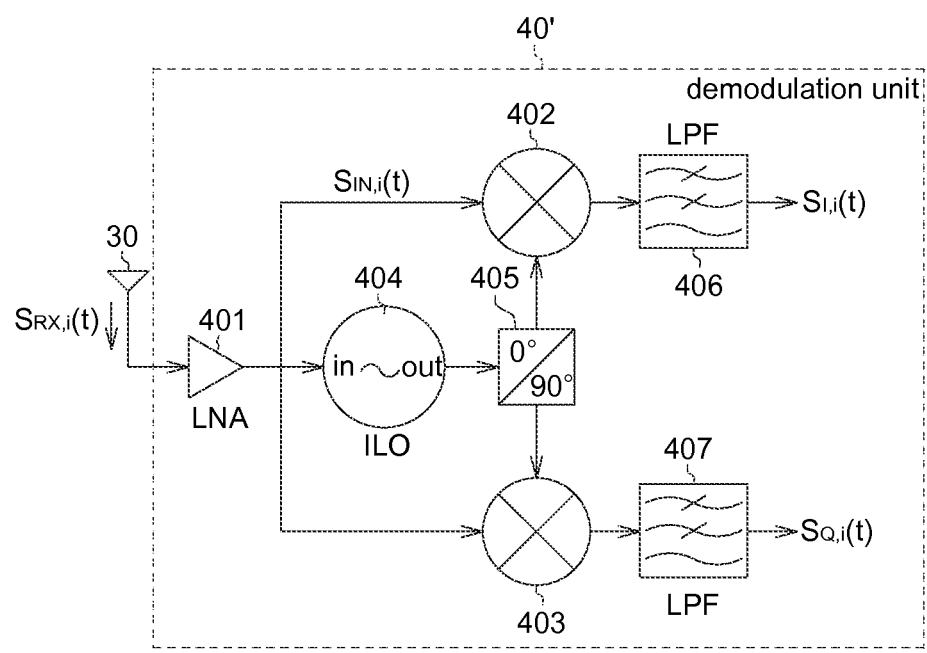
FIG. 4C shows a demodulation unit according to still another exemplary embodiment of the disclosure.

In one embodiment, as shown in FIG. 4C, the demodulation unit 40' includes a low noise amplifier unit (LNA) 401, two mixer units 402 and 403, an oscillator unit 404, a 90° power splitter unit 405 and two low-pass filter units 406 and 407.

The low noise amplifier unit 401 receives the detection signal from the receiving unit 30 (using antenna as example). The output ports of the low noise amplifier unit 401 are coupled to or electrically connected to the input ports of the mixer units 402, 403 and the injection port of the oscillator unit 404, respectively. The oscillator unit 404 is under a self-injection locking mode due to the output signal $S_{IN,i}(t)$ of the low noise amplifier unit 401. When the frequency of the output signal $S_{IN,i}(t)$ is different from the initial oscillation frequency of the oscillator unit 404, after injection locking, the output signal frequency of the oscillator unit 404 will be same as the frequency of the output signal $S_{IN,i}(t)$. There is a time delay between the output signal of the oscillator unit 404 and the input signal $S_{IN,i}(t)$. With this time delay, the oscillator unit 404 functions as a band-pass filter with a tunable center frequency for supporting multiple users based on a frequency-division multiple access (FDMA) technique. The oscillator unit 404 is coupled to or electrically connected to the input port of the 90° power splitter unit 405. The 90° power splitter unit 405 output two signals (which are in quadrature phase to each other) to the mixer units 402 and 403. In one embodiment, the 90° power splitter unit 405 outputs in-phase signals and quadrature-phase signals to the mixer units 402 and 403.

The output port of the mixer units 402 and 403 are coupled to or electrically connected to the input port of the low-pass filter units 406 and 407. After signal processing of the outputs $S_{I,i}(t)$ and $S_{Q,i}(t)$ of the low-pass filter units 406 and 407, the frequency demodulation is accomplished and the baseband output signal is generated. The signal processing function for example is $\tan^{-1}((S_{I,i}(t))/(S_{Q,i}(t)))$, wherein "i" is the index parameter of the receiver, and "t" is a time parameter.

Figure 6:
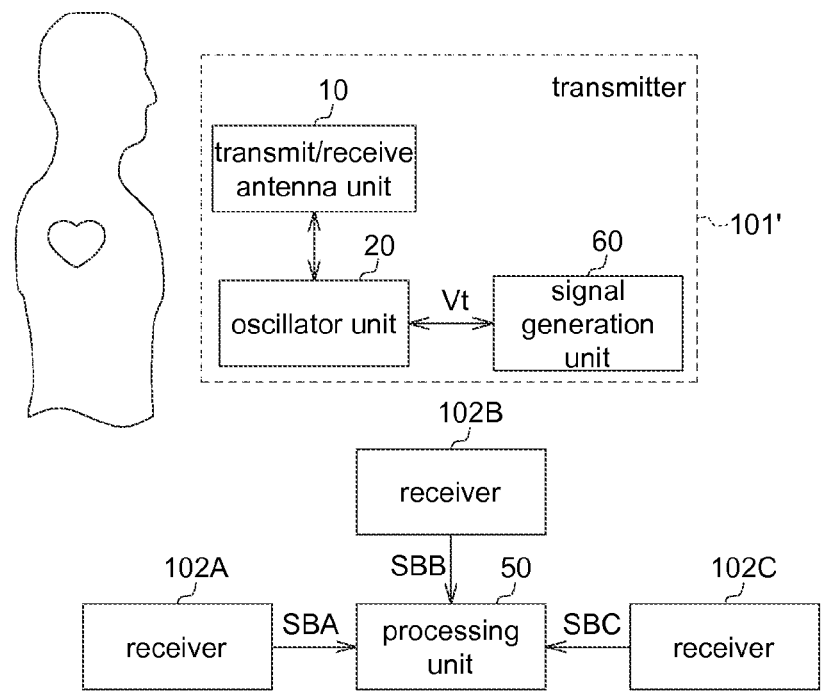
FIG. 6 shows a block diagram of a motion/vibration detection system according to an exemplary embodiment of the disclosure.

In one embodiment, as shown in FIG. 6, the frequency modulation signals generated by the transmitter 101' will be received and demodulated by the receivers 102A-102C. The position (for example, but not limited to, the indoor position information, and so on) of the transmitter could be extracted from the phase difference between the output baseband signals from the receivers 102A-102C.

The receivers 102A, 102B and 102C receive the radio frequency modulation signal from the transmitter 101'. The receivers demodulate the frequency modulation signal into baseband signals, and output baseband signals SBA~SBC to the processing unit 50. The frequency modulation signal from the transmitter 101' is generated due to Doppler modulation of the motion/vibration (for example, cardiopulmonary activity) of the user and frequency modulation of the analog control voltage waveform Vt. After the processing unit 50 performs digital band-pass filtering, amplification of the baseband signals SBA~SBC and determination of the phase difference of baseband signals SBA~SBC, the processing unit 50 could obtain the position of the object under detection. In addition, after the processing unit 50 performs digital low-pass filtering, amplification and Fourier transformation on the baseband signals SBA~SBC, the processing unit 50 could obtain the time-domain waveform and frequency of the motion/vibration signal (for example, the cardiopulmonary signals).

In this embodiment, for example, the transmitter 101' is worn on the chest of the user under detection. By so, the position of the user and the motion/vibration signal (for example, the cardiopulmonary signals) of the user are detected. The signal generation unit 60 of the transmitter 101' is coupled to or electrically connected to the voltage input port of the oscillator unit 20. The signal generation unit 60 generates the analog control voltage waveform Vt, which causes the oscillator unit 20 to generate frequency modulation signal. In the embodiment, if the receivers 102A, 102B and 102C are designed as shown in FIG. 4A, the amplitude of the baseband signals SBA, SBB and SBC will be about the same. It is because the oscillator units (not shown in the FIG. 6) of the receivers 102A, 102B and 102C will output the received detection signal (STX) with the same amplitude. If the receivers 102A, 102B and 102C are designed as shown in FIG. 4B or FIG. 4C, the amplitude of the baseband signals SBA, SBB and SBC will be different.

In this embodiment, the distance between the transmit/receive antenna unit 10 and the receiving units (not shown in FIG. 6) of the receivers 102A, 102B and 102C are different and thus the receiving units have different time delay on receiving the detection signal. The time delay will be reflected on the baseband signals SBA, SBB and SBC of the receivers 102A, 102B and 102C. In this embodiment, the output ports of the receivers 102A, 102B and 102C are coupled to or electrically connected to the processing unit 50. The processing unit 50 receives the baseband signals SBA, SBB and SBC, compares the phase difference between the baseband signals, to obtain the time delay of the receivers 102A, 102B and 102C on receiving the detection signal. The processing unit 50 could obtain the position of the transmit/receive antenna unit 10 (i.e. the position of the user under measurement) according to the position of the receiving units. In addition, the baseband signals SBA, SBB and SBC could include the motion/vibration signal (for example, but not limited to, breath, heartbeat, throat vibration, body vibration, and so on). After digital filtering and Fourier transformation, the time-domain waveform and frequency of the motion/vibration signals are obtained.

Figure 7:
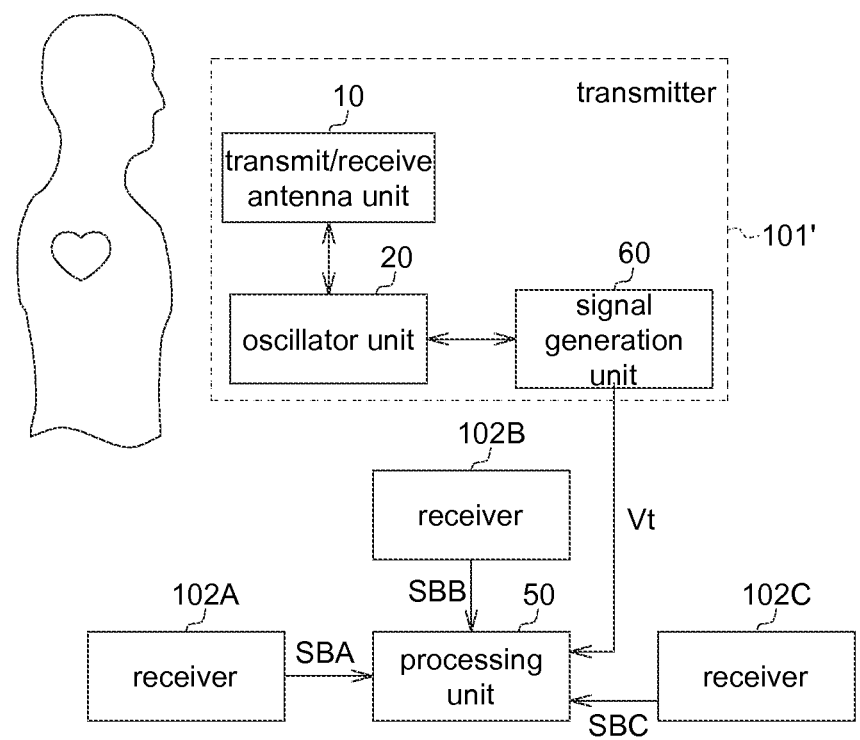
FIG. 7 shows a block diagram of a motion/vibration detection system according to an exemplary embodiment of the disclosure.

In one embodiment, as shown in FIG. 7, in the transmitter 101', the analog control voltage waveform Vt generated by the signal generation unit 60 is coupled to or electrically connected to the processing unit 50. In this embodiment, the transmitter 101' is synchronous with the receivers 102A~102C because of injection locking. The distance between the transmit/receive antenna unit 10 and the receivers 102A~102C can be obtained from the arrival time differences of the detection signals received by the receivers 102A~102C by comparing the phase difference of the baseband signals SBA, SBB and SBC of the receivers 102A~102C. The position information of the user under detection can be obtained.

In addition to TDoA (Time Difference of Arrival) described above, other position technology or combination of position technologies could be used. Below is several positioning methods and their brief description, but it is not to limit the disclosure. For example, the RSS (received signal strength) technology calculates the transmitter position according to (1) the signal strength received by different receivers and (2) a propagation equation (which expresses that the received signal power is in reverse relation with the square of the distance). The ToA (Time of Arrival) technology uses the time which the transmitter is frequency modulated (when the transmitter circuit receives the analog control voltage waveform) as an initial point. After the baseband output signal demodulated in the receiver is compared with the analog control voltage waveform, the signal travel time from the transmitter to each receiver is obtained, and the position of the transmitter is calculated. In the AoA (Angle of Arrival) technology, implementing the receiving unit of the receiver as a receiving antenna array, antenna beams can be scanned. The position of the transmitter is obtained under the case that two receivers receive the baseband output signals simultaneously.

Figure 8:
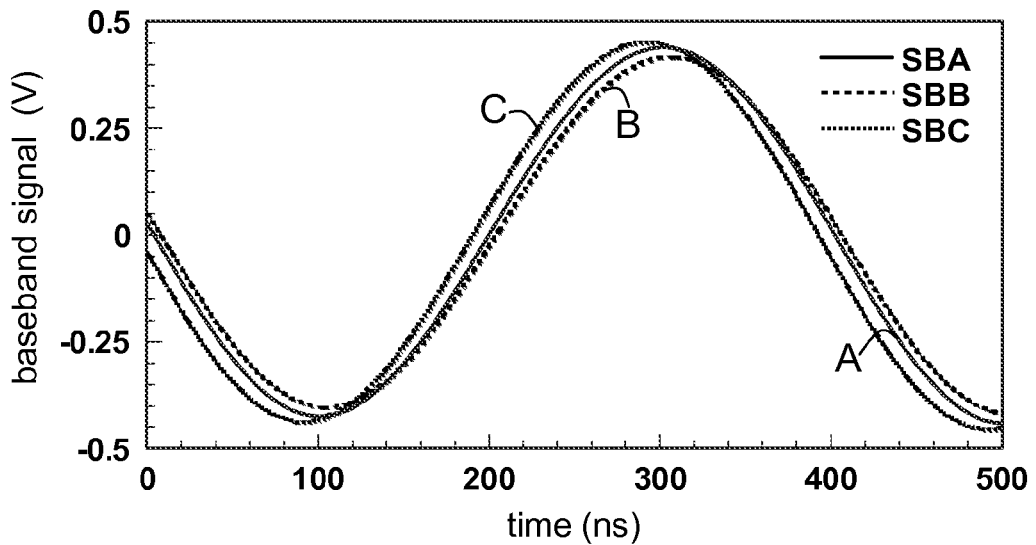
FIG. 8 shows a baseband wave pattern according to an experimental result.

FIG. 8 is corresponding to the experimentation in FIG. 6. The position of the user under detection is (3.2, 4.5), the position of receiver 102A is (0,0), the position of receiver 102B is (8,0), and the position of receiver 102C is $(4, 4^{\sqrt{3}})$. The oscillator unit 20 is operated at 2.45 GHz and the signal generation unit 60 generates a sine wave having 2.5 MHz frequency and 1 Vp-p amplitude. Accordingly, the oscillator unit 20 generates a frequency modulation signal having 1 MHz frequency deviation and 2.5 MHz modulation rate. The baseband signal of the receiver is as shown in FIG. 8. The phase difference between SBA and SBB is 3.51°, the phase difference between SBB and SBC is −12.15° and the phase difference between SBC and SBA is 8.64°. The obtained position information is (3.1146, 4.4954) which is very close to the real position of the object.

Figure 9:
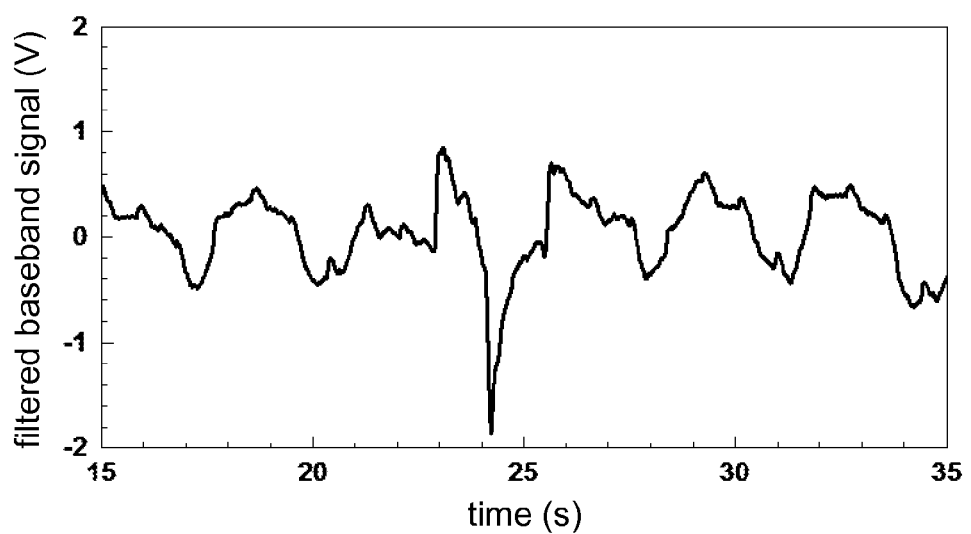
FIG. 9 shows a time domain wave pattern according to an experimental result.
Figure 10:
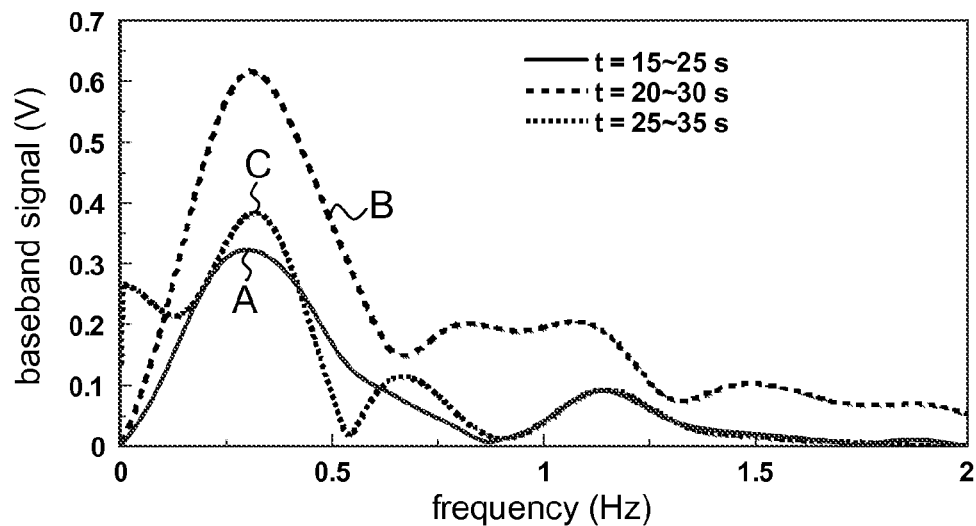
FIG. 10 shows a spectrum according to an experimental result according to an embodiment of the disclosure.
Figure 11:
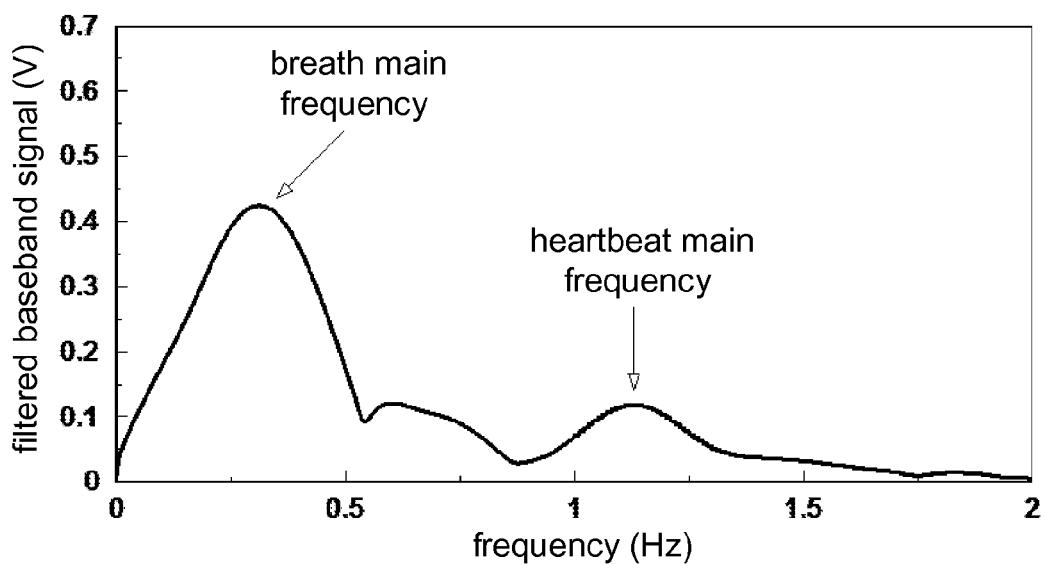
FIG. 11 shows a spectrum according to an experimental result according to an embodiment of the disclosure.

FIG. 9 shows a time domain wave pattern according to an experimental result. FIG. 10 shows a spectrum according to an experimental result according to an embodiment of the disclosure. FIG. 11 shows a spectrum according to an experimental result according to an embodiment of the disclosure. The time domain waveforms shown in FIG. 9 include breath, heartbeat, and body motion information.

After Fourier transformation, the spectrum of different time interval is shown in FIG. 10. The full line A, the dashed line B and the dotted line C in FIG. 10 represent the spectrum in 15~25 seconds, in 20~30 seconds and in 25~35 seconds, respectively. The spectrum in 23~26 second of FIG. 9 shows unstable cardiopulmonary signals, which is caused by the user's fidgeting movements during the detection. In the experimentation, the spectra of these three different time periods are multiplied and one third power of this spectral product is calculated. The result is shown in FIG. 11. It is recognizable that the frequency of breath and heartbeat is 0.31 Hz and 1.13 Hz, respectively, that is, 19 breath counts/minute and 69 heartbeat counts/minute. It is very close to the detection result of other medical instruments.

In another embodiment, the motion/vibration detection method includes: transmitting a detection signal from a transmitter; reflecting the detection signal into at least one reflected detection signal (SRX) by at least one object; receiving the at least one reflected detection signal (SRX) by the transmitter with an oscillator unit entering into a self-injection locking mode; receiving the detection signal by a receiver; and frequency demodulating the received detection signal by the receiver into a baseband output signal, to extract at least one motion/vibration information of the at least one object.

In another embodiment, a processing unit processes the received baseband signal to extract the at least one motion/vibration information or external vibration information. In another embodiment, the processing unit receives multiple baseband output signals from multiple receivers, compares the phase difference between the baseband output signals, calculates the arrival time differences of the multiple receivers, and obtains the position of the transmitter.

The embodiments of the motion/vibration detection method could be understood by referencing the embodiments of the motion/vibration detection system.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A motion/vibration detection system, comprising:
at least one transmitter, the at least one transmitter comprising a transmit/receive antenna unit and a first oscillator unit; and
at least one receiver, comprising a receiving unit and a demodulation unit; wherein,
the transmit/receive antenna unit is coupled to or electrically connected to a signal output port of the first oscillator unit, receives an output signal from the first oscillator unit and transmits a detection signal;
the detection signal is reflected from at least one object as a reflected detection signal, which is received by the transmit/receive antenna unit;
the transmit/receive antenna unit injects the reflected detection signal, as an injection signal, into the first oscillator unit and accordingly the first oscillator unit is under a self-injection locking mode;
the receiving unit is coupled to or electrically connected to the demodulation unit and receives the detection signal; and
the demodulation unit demodulates the detection signal received by the receiving unit into a baseband output signal, to extract at least one motion/vibration information of the at least one object.

2. The motion/vibration detection system of claim 1, further comprising:
a processing unit, coupled to or electrically connected to the demodulation unit, for receiving the baseband output signal from the demodulation unit;
the processing unit processes the baseband output signal to extract the at least one motion/vibration information of the at least one object.

3. The motion/vibration detection system of claim 2, wherein,
the processing unit performs digital band-pass filtering, amplifying, and analyzing a phase difference of the baseband output signal, and obtains a position information of the at least one object.

4. The motion/vibration detection system of claim 2, wherein,
the processing unit performs digital low-pass filtering, amplifying, and Fourier-transform on the baseband output signal, and obtains time-domain waveforms and frequencies of the at least one motion/vibration information.

5. The motion/vibration detection system of claim 2, wherein,
the processing unit receives a plurality of baseband output signals from a plurality of receivers, compares a phase difference of the plurality of baseband output signals, calculates arrival time differences of the plurality of receivers, and obtains a position of the at least one transmitter.

6. The motion/vibration detection system of claim 2, wherein,
the at least one transmitter further comprises comprising a signal generation unit, which is coupled to or electrically connected to the first oscillator unit; and
the signal generation unit generates an analog control voltage waveform, and inputs the analog control voltage waveform into the first oscillator unit and the processing unit.

7. The motion/vibration detection system of claim 6, wherein, the demodulation unit demodulates the detection signal into a voltage signal containing the analog control voltage waveform and the at least one motion/vibration information.

8. The motion/vibration detection system of claim 1, further comprising:
a signal generation unit, coupled to or electrically connected to a voltage input port of the first oscillator unit.

9. The motion/vibration detection system of claim 1, wherein the transmit/receive antenna unit comprises:
a first antenna, transmitting the detection signal, and receiving the reflected detection signal;
the first antenna is a single antenna or an antenna array.

10. The motion/vibration detection system of claim 1, wherein the transmit/receive antenna unit comprises:
a first antenna, transmitting the detection signal; and
a second antenna, receiving the reflected detection signal;
each of the first antenna and the second antenna is a single antenna or an antenna array.

11. The motion/vibration detection system of claim 10, wherein the receiving unit comprises:

a third antenna, receiving the detection signal;
the third antenna is a single antenna or an antenna array.

12. The motion/vibration detection system of claim 1, wherein the first oscillator unit is an optical laser, and the transmit/receive antenna unit comprises:
   an optical transmitting device, transmitting a laser output optical signal of the first oscillator unit as the detection signal; and
   an optical receiving device, injecting the reflected detection signal into the first oscillator unit.

13. The motion/vibration detection system of claim 1, wherein, the injection signal is injected into an injection signal input port of the first oscillator unit, and accordingly the first oscillator unit is under the self-injection locking mode.

14. The motion/vibration detection system of claim 1, wherein, the injection signal is injected into one of a pair of differential signal output ports of the first oscillator unit, and accordingly the first oscillator unit is under the self-injection locking mode.

15. The motion/vibration detection system of claim 1, wherein,
   the injection signal is injected into a single-ended signal output port of the first oscillator unit, and accordingly the first oscillator unit is under the self-injection locking mode.

16. The motion/vibration detection system of claim 1, wherein,
   the detection signal and the reflected detection signal are both a radio frequency modulation signal.

17. The motion/vibration detection system of claim 1, wherein, the demodulation unit comprises:
   a second oscillator unit, a time delay unit, a mixer unit and a low-pass filter unit;
   the receiving unit is coupled to or electrically connected to one input port of the second oscillator unit, injects the detection signal into the second oscillator unit, and accordingly the second oscillator unit is injection-locked by the detection signal;
   two output ports of the second oscillator unit are coupled to or electrically connected to the time delay unit and the mixer unit, respectively;
   two input ports of the mixer unit are coupled to or electrically connected to at least one of the two output ports of the second oscillator unit and an output port of the time delay unit, an output port of the mixer unit is coupled to or electrically connected to an input port of the low-pass filter unit;
   the mixer unit and the time delay unit demodulate an output signal of the second oscillator unit; and
   the low-pass filter unit filters out mixing spurious signals from an output signal of the mixer unit, and an output of the low-pass filter unit is the baseband output signal of the demodulation unit.

18. The motion/vibration detection system of claim 17, wherein,
   the output signal of the second oscillator unit is synchronous with the detection signal because of injection locking.

19. The motion/vibration detection system of claim 1, wherein,
   the demodulation unit comprises: an amplifier unit a mixer unit, a time delay unit and a low-pass filter unit;
   the amplifier unit is coupled or electrically connected to the receiver unit;
   the time delay unit is coupled or electrically connected to the amplifier unit;
   two input ports of the mixer unit are coupled to or electrically connected to the amplifier unit and the time delay unit; and
   the low-pass filter unit is coupled to or electrically connected to an output port of the mixer unit.

20. The motion/vibration detection system of claim 1, wherein,
   the demodulation unit comprises: a low noise amplifier unit, a first mixer unit, a second mixer unit, a second oscillator unit, a 90° power splitter unit, a first low-pass filter unit and a second low-pass filter unit;
   the low noise amplifier unit receives the detection signal from the receiving unit, and an output port of the low noise amplifier unit is coupled to or electrically connected to an input port of the first mixer unit, an input port of the second mixer unit and an injection port of the second oscillator unit;
   the second oscillator unit receives a signal from the low noise amplifier unit, and the second oscillator unit is injection-locked by the received signal from the low noise amplifier unit;
   the second oscillator unit is coupled to or electrically connected to an input port of the 90° power splitter unit;
   the 90° power splitter unit is coupled to or electrically connected to the first mixer unit and the second mixer unit, and outputs in-phase signals and quadrature-phase signals to the first mixer unit and the second mixer unit;
   an output port of the first mixer unit is coupled to or electrically connected to an input port of the first low-pass filter unit, and an output port of the second mixer unit is coupled to or electrically connected to an input port of the second low-pass filter unit; and
   the baseband output signal is generated according to a signal processing function on the output of the first low-pass filter unit and the output of the second low-pass filter unit.

21. The motion/vibration detection system of claim 20, wherein,
   the signal processing function for generating the baseband output signal is expressed as $\tan^{-1}((S_{1,i}(t))/(S_{2,i}(t)))$, where "i" is an index parameter of the receiver, t is a time parameter, $S_{1,i}(t)$ is the output of the first low-pass filter unit, and $S_{2,i}(t)$ is the output of the second low-pass filter unit.

22. A motion/vibration detection method, adapted to a motion/vibration detection system, comprising:
   transmitting a detection signal from a transmit/receive antenna unit, wherein the transmit/receive antenna unit is coupled to or electrically connected to a signal output port of an oscillator unit;
   making the detection signal reflect from at least one object to become at least one reflected detection signal;
   receiving the at least one reflected detection signal by the transmit/receive antenna unit;
   injecting the reflected detection signal, from the transmit/receive antenna unit, as an injection signal, into the oscillator unit so that the oscillator unit is under a self-injection locking mode;
   receiving the detection signal by a receiver; and
   demodulating the detection signal received by the receiver into a baseband output signal, to extract at least one motion/vibration information of the at least one object.

23. The motion/vibration detection method of claim 22, further comprising: processing the received baseband output signal by a processing unit, to extract the at least one motion/vibration information of the at least one object.

24. The motion/vibration detection method of claim 23, wherein, the processing unit receives a plurality of baseband output signals from a plurality of receivers, compares phase differences of the plurality of baseband output signals, and calculates arrival time differences of the plurality of receivers, to obtain a position of the transmit/receive antenna unit.

* * * * *